(12) United States Patent
Shown et al.

(10) Patent No.: US 9,790,175 B2
(45) Date of Patent: Oct. 17, 2017

(54) PROCESS FOR THE REMOVAL OF SODIUM FROM DI-SULFIDE OIL

(71) Applicant: Reliance Industries Limited, Mumbai (IN)

(72) Inventors: Biswajit Shown, West Bengal (IN); Nagarathinam Shenbaga Murthy, Tuticorin (IN); Asit Kumar Das, Faridabad (IN); Swapan Ghosh, Navi Mumbai (IN); Bidhayak Das, West Bengal (IN); Rajeshwer Dongara, Navi Mumbai (IN); Anirban Ray, West Bengal (IN); Chirag Dalpatbhai Panseriya, Gujarat (IN); Udayan Sivathanu Ramalakshmi, Tamilnadu (IN); Atul Kathiria, Jamnagar (IN)

(73) Assignee: Reliance Industries Limited, Mumbai (IN)

( * ) Notice: Subject to any disclaimer, the term of this patent is extended or adjusted under 35 U.S.C. 154(b) by 0 days.

(21) Appl. No.: 15/121,535

(22) PCT Filed: Mar. 13, 2015

(86) PCT No.: PCT/IB2015/051846
§ 371 (c)(1),
(2) Date: Aug. 25, 2016

(87) PCT Pub. No.: WO2015/136491
PCT Pub. Date: Sep. 17, 2015

(65) Prior Publication Data
US 2016/0362363 A1 Dec. 15, 2016

(30) Foreign Application Priority Data
Mar. 14, 2014 (IN) .......................... 852/MUM/2014

(51) Int. Cl.
*C07C 319/30* (2006.01)

(52) U.S. Cl.
CPC ................... *C07C 319/30* (2013.01)

(58) Field of Classification Search
CPC .................................................... C07C 319/30
See application file for complete search history.

(56) References Cited

U.S. PATENT DOCUMENTS 7,342,145 B2  3/2008  Wu et al.

FOREIGN PATENT DOCUMENTS

WO     2005111175 A1    11/2005

OTHER PUBLICATIONS

International Search Report issued in corresponding application No. PCT/IB2015/051846 mailed Aug. 13, 2015 (3 pages).
Written Opinion of the International Searching Authority issued in corresponding application No. PCT/IB2015/051846 mailed Aug. 13, 2015 (6 pages).
M.S. Patil et al., "Unsteady State Adsorption—Column Studies"; International Journal of Advanced Engineering Research and Studies; vol. 1, Issue II, pp. 179-184; Jan.-Mar. 2012 (6 pages).

*Primary Examiner* — Rosalynd Keys
(74) *Attorney, Agent, or Firm* — Osha Liang LLP

(57) ABSTRACT

In the present disclosure there is provided a process for obtaining di-sulfide oil having sodium level below 0.1 ppm wherein a stream comprising di-sulfide oil having sodium level 1 ppm, collected as a waste stream from LPG desulfurization unit, is passed through an alumina bed packed in a column at a pre-determined liquid hourly space velocity (LHSV) and at pre-determined temperature to obtain a treated stream comprising di-sulfide oil having sodium level below 0.1 ppm.

9 Claims, No Drawings

PROCESS FOR THE REMOVAL OF SODIUM FROM DI-SULFIDE OIL

FIELD OF THE DISCLOSURE

The present disclosure relates to a process for obtaining di-sulfide oil having sodium level below 0.1 ppm.

BACKGROUND

Di-sulfide oil (sulfur oil) is a low value by-product of Liquefied Petroleum Gas (LPG) desulfurization process. During the LPG desulfurization process, LPG laden with mercaptan is treated with NaOH solution in the presence of a homogeneous catalyst to extract mercaptans from the LPG. The di-sulfide oil which is produced as a waste or as a by-product stream during the LPG desulfurization process comprises a relatively high concentration of sodium which makes the di-sulfide oil inappropriate for a number of applications. The relatively high concentration of sodium may be due to the presence of unreacted R—S—Na or due to micro-emulsion formation of R—S—S—R with NaOH solution. The di-sulfide oil obtained from the LPG desulfurization process is sent to a hydrotreater for further processing as a low value stream. Notwithstanding the fact that the di-sulfide oil comprises a relatively high concentration of sodium, the presence of a minimum of 60% sulfur makes it a potential substitute for a number of sulfur containing high value chemical compounds which are used in a number of applications. However, the presence of a relatively high concentration of sodium prevents its use in other applications.

EXISTING KNOWLEDGE

Among the miscellaneous applications known for sulfur containing compounds, their use as an additive for reducing/preventing the formation of coke on the surface of metallic coils of cracking reactors is a highly desirous application. Further, their use as a sulfiding/pre-sulfiding agent for catalysts used in hydrocrackers and hydrotreaters in refineries and in the hydro-processing of non-edible vegetable oils to produce biofuels is also well-known. Among various sulfur containing compounds known to be used as anti-coking additives and/or sulfiding agents, the use of dialkyl sulfide and dialkyl disulfides is well known. However, the major disadvantage associated with the use of such compounds is their high cost. Further, proper care is also recommended for commercial trials thereof so as to avoid their detrimental effects on the downstream processes.

A PCT Publication No. 2005/111175 discloses the use of sulfur oil which is a mixture of organic disulfides having $C_2$-$C_4$ for inhibiting coke formation on the surface and/or coils of a pyrolysis furnace. The sulfur oil used in the process of the aforementioned PCT application is a low value product obtained from LPG Mercaptan oxidation units and comprises relatively high concentration of sodium (around 1 ppm). The presence of relatively high level of sodium in the sulfur oil can be detrimental to the reactions wherein the sulfur oil is used.

In the thermal cracking process when di-sulfide oil (sulfur oil) is used as an anti-coking agent, higher amount of sodium i.e. ($\geq$1 ppm) contained therein, forms sodium oxide and deposits on the surface of the heater tube as a passive layer which inhibits heat transfer and results in coke formation on the heater tube. In the hydrothermal reactor, high amount of sodium present in the di-sulfide oil reacts with the hydrothermal cracking catalyst and forms a sodium aluminate layer on catalyst active sites. Alternatively, sodium reacts with active metals present in the catalyst composition and forms an alloy which eventually leads to reduced catalytic activity.

Therefore, in spite of being established as an excellent economical alternative to the conventionally known anti-coking agents and sulfiding agents, the presence of sodium at around 1 ppm level in the di-sulfide oil prevents its further use.

Therefore, there is felt a need to provide a process for the removal of sodium from di-sulfide oil (sulfur oil) produced as a waste or as a by-product stream during the LPG desulfurization process in order to provide an alternative to the existing sulfur containing compounds which is economical and process benign for a number of applications.

OBJECTS

Some of the objects of the present disclosure, which at least one embodiment is adapted to provide, are described herein below:

It is an object of the present disclosure to ameliorate one or more problems of the prior art or to at least provide a useful alternative.

Another object of the present disclosure is to provide a process for obtaining di-sulfide oil (sulfur oil) having sodium level below 0.1 ppm, the di-sulfide oil being obtained as a waste or as a by-product stream from the LPG desulfurization process.

Still another object of the present disclosure is to provide a process for obtaining di-sulfide oil having sodium level below 0.1 ppm; the process being very simple, efficient and economical.

Yet another object of the present disclosure is to provide a useful and economical alternative to the existing anti-coking additives and sulfiding agents which are used in a number of processes including, but not limited to, hydrotreating and hydro-processing.

Other objects and advantages of the present invention will be more apparent from the following description which is not intended to limit the scope of the present invention.

SUMMARY

In one aspect the present disclosure provides a process for obtaining di-sulfide oil having sodium level below 0.1 ppm, said process comprising passing a stream comprising di-sulfide oil having sodium level of 1 ppm through an alumina bed packed in a column, at a liquid hourly space velocity (LHSV) ranging from 0.5 to 5.0 hr$^{-1}$ and at a pre-determined temperature to obtain a treated stream comprising di-sulfide oil having sodium level below 0.1 ppm.

The liquid hourly space velocity (LHSV) can range from 0.5 to 2 hr$^{-1}$.

In one embodiment, the liquid hourly space velocity (LHSV) ranges from 1.0 to 1.5 hr$^{-1}$.

The pre-determined temperature can vary from 10 to 40° C.

In one embodiment, the pre-determined temperature varies from 20 to 30° C.

The treated stream comprising di-sulfide oil can have sodium level below 0.05 ppm.

In one embodiment, the treated stream comprising di-sulfide oil has sodium level below 0.02 ppm.

In another embodiment, the treated stream comprising di-sulfide oil has sodium level of 0.01 ppm.

Typically, the alumina is characterized by the following properties: average particle size ranging from 0.3 to 0.7mm; pore volume ranging from 44.1 to 71.9 cm$^3$/100 g; surface area ranging from 195 to 331 m$^2$/g and density ranging from 543 to 829 kg/m$^3$.

DETAILED DESCRIPTION

As described herein above, a stream comprising di-sulfide oil, obtained as a waste or as a by-product stream during the LPG desulfurization process, comprises a relatively high concentration of sodium which makes it unacceptable for a number of applications such as use as an anti-coking agent in thermo-cracking processes. The present process described herein below reduces the sodium content in di-sulfide oil streams to an amount which is even lower than the standard acceptable range of 1 ppm; thereby making the di-sulfide oil useful for a number of applications. Thus, the disadvantages associated with the use of expensive sulfur containing compounds such as dialkyl disulfides, dialkyl sulfides and di-sulfide oil which comprise relatively higher concentration of sodium are advantageously alleviated by means of the process of the present disclosure.

The process of the present disclosure is most suitable for reducing the sodium content of the di-sulfide oil streams originally having sodium content of about 1 ppm. In the event the di-sulfide oil stream has sodium content of more than 1 ppm, it is first made to undergo treatment in one way or the other, to obtain a stream having sodium content of about 1 ppm. The means of treatment mentioned herein above, in one embodiment, include processes such as dilution where the high sodium concentration stream is diluted with a low sodium concentration stream to yield a stream having an intermediate or the desired sodium concentration.

In one aspect, the present disclosure provides a process for obtaining di-sulfide oil having sodium level below 0.1 ppm; the process comprising the steps of obtaining a stream comprising di-sulfide oil having sodium level of 1 ppm from LPG desulfurization units and passing the stream through an adsorbent bed under pre-determined operating conditions of volume, time and temperature to obtain a treated stream that comprises di-sulfide oil having sodium level below 0.1 ppm.

Typically, the di-sulfide oil streams are obtained as a waste or a by-product stream from LPG desulfurization process. Further, the di-sulfide oil in accordance with present disclosure comprises at least one $C_2$-$C_4$ containing alkyl disulfides selected from the group consisting of dimethyl disulfide, ethyl methyl disulfide, diethyl disulfide and the like.

The adsorbent used in the process of the present disclosure is an inorganic oxide based adsorbent. Example of inorganic oxide based adsorbent suitable for the process of the present disclosure includes alumina. The inventors of the present disclosure have used multiple varieties of alumina which differ in their characteristic attributes such as density, pore volume and surface area in order to optimize the process of the present disclosure. The alumina which is useful for the purpose of the present disclosure is activated alumina with high adsorption capacity owing to its specific surface area and tailored pore size distribution.

The alumina used in the process of the present disclosure is characterized by the following properties: average particle size ranging from 0.3 to 0.7mm; pore volume ranging from 44.1 to 71.9 cm$^3$/100 g; surface area ranging from 195 to 331 m$^2$/g and density ranging from 543 to 829 kg/m$^3$. Further, the alumina used in the process of the present disclosure may be of different shapes such as spheres, extrudates, granules and rings.

In an experimental version of the present process, the alumina adsorbent is packed in a glass column fitted with a flow control stop cock. The stream comprising the di-sulfide oil is stored in a separating funnel provided at the top of the glass column. The stream is then passed though the column packed with the alumina adsorbent at a pre-determined liquid hourly space velocity and at a pre-determined temperature. The liquid hourly space velocity (LHSV) typically ranges from 0.5 to 5 hr$^{-1}$. In accordance with one of the embodiments of the present disclosure, the liquid hourly space velocity ranges from 0.5 to 2 hr$^{-1}$. In accordance with another embodiment, the liquid hourly space velocity (LHSV) ranges from 1.0 to 1.5 hr$^{1-1}$. The liquid hourly space velocity of the stream passing through the column packed with the alumina adsorbent is controlled though the column and the separating funnel stoppers. The pre-determined temperature typically ranges from 10 to 40° C. In accordance with one of the embodiments of the present disclosure, the temperature ranges from 20 to 30° C.

The stream passing though the column packed with the alumina adsorbent is collected at every 2 hour interval (hereinafter referred to as a treated stream) and subjected to atomic absorption spectroscopy (AAS) and inductively coupled plasma mass spectroscopy (ICPMS) analysis to measure the sodium level. The sodium level of the original oil stream—the waste or the by-product stream as collected from LPG desulfurization units is also measured by AAS. Typically it is 1 ppm.

AAS and ICPMS results show that the amount of sodium in the treated stream is below 0.1 ppm. In some experiments, the amount of the sodium in the treated stream was found to be below 0.05 ppm, in some other experiments it was found to be below 0.02 ppm and in some other, 0.01 ppm.

The alumina based adsorbent used in the process of the present disclosure demonstrates excellent adsorption efficiency for the sodium metal present in the di-sulfide oil. The sodium removal efficiency of the alumina adsorbent typically ranges from 98.7 to 99.7%. Further, the alumina based adsorbent is capable of treating the di-sulfide oil which is at least 200 times the volume of alumina used.

The efficiency of the treated stream containing di-sulfide oil having sodium level below 0.1 ppm was evaluated in a number of applications that include, but are not limited to, its use as an anti-coking additive in the thermal cracking process, as a sulfiding agent for the pre-sulfidization of catalysts used in the hydro-treating and hydro-cracking process and in the hydrogenation of non-edible vegetable oils to produce bio-fuels.

The embodiments herein and the various features and advantageous details thereof are explained with reference to the non-limiting embodiments in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

EXAMPLE-1

Process for Reducing Sodium Content in the Di-sulfide Oil in Accordance with the Present Disclosure A stream comprising di-sulfide oil (sulfur oil), produced as a waste or as a by-product stream from mercaptan oxidation units of a refining complex was used in the following examples. Various properties of the stream are presented in Table 1.

TABLE 1

Characteristic properties of the di-sulfide oil (sulfur oil) used in the present process

| Sr. No | Attributes | Unit of measurement | Value |
|---|---|---|---|
| 1 | Appearance | — | Clear with nil particulates |
| 2 | Total Sulfur | wt % | 60.0 typical |
| 3 | Critical temperature | Deg C. | 351 |
| 4 | Critical pressure | , bars | 47.8 |
| 5 | Boiling range | ° C. | 110-180 |
| 6 | Density (20deg C.) | g/cc | 1.03 |
| 7 | Viscosity (20deg C.) | cps | 0.597 |
| 8 | Vapor pressure (20deg C.) | mbar | 13.6 |
| 9 | Surface tension (20deg C.) | dynes/cm | 33.6 |
| 10 | Specific heat (25deg C.) | KJ/Kg-K | 1.521 |
| 11 | Sodium (Na) | ppm w | 1.0 max |
| 12 | Cobalt (Co) | ppm | 0.25 max |
| 13 | Copper (Cu) | ppm | 0.10 max |
| 14 | Iron (Fe) | ppm | 0.20 max |

The oil obtained from mercaptan oxidation units of a refining complex was stored in a 1 liter separating funnel located at the top of a glass column (45 cm height and 3.2 cm diameter) containing alumina. 30 g (~48 ml) of alumina ($A_1$) was poured into the glass column having a flow control stop cock. The alumina having the following characteristic attributes was used: average particle size: 0.5 mm; density: 629 kg/m$^3$; pore volume: 68.9 cm$^3$/100 g and surface area: 195 m$^2$/g. The oil stream contained in the funnel was passed through the column at ambient temperature (25° C.) with a liquid hourly space velocity (LHSV) of 1.25 h$^{-1}$. The LHSV was controlled through the funnel and column stoppers. The stream after passing though the alumina bed (referred to as a treated stream) was collected at every 2 hours interval and subjected to AAS (atomic absorption spectroscopy) and inductively coupled plasma mass spectroscopy (ICPMS) for the measurement of Na level.

The amount of Na in the treated sample was found to be 0.01 ppm.

EXAMPLE-2

Process for Reducing Sodium Content in Di-sulfide Oil in Accordance with the Present Disclosure In this example, the treatment of the di-sulfide oil was carried out in the same manner as described in Example-1, except that the alumina adsorbent that was used, had higher density, lower pore volume and lower surface area ($A_2$) [as compared to the alumina used in Example 1 ($A_1$)]. Characteristic attributes of the alumina adsorbent used in the present Example ($A_2$) are provided herein under, in Table-2.

TABLE 2

Characteristic features of the alumina used in examples 1, 2 and 3:

| Typical Characteristics | Unit of measurement | Alumina adsorbent $A_1$ | Alumina adsorbent $A_2$ | Alumina adsorbent $A_3$ |
|---|---|---|---|---|
| $Al_2O_3$ | wt % | 93.5 min. | 93.5 min. | 93.5 min. |
| $Na_2O$ | ppm (w) | 3200 max. | 3200 max. | 3200 max. |
| Shape | — | beads | beads | extrudates |
| Average particle size | mm | 0.5 | 0.5 | 0.5 |
| Density | DRT kg/m$^3$ | 629 | 829 | 543 |
| Total porous volume | VPT cm$^3$/100 g | 68.9 | 44.1 | 71.9 |
| Mechanical strength | EGG daN | 5.3 | 12.1 | 1.4/mm |
| Surface area | BET m$^2$/g | 195 | 331 | 320 |
| Loss on ignition (300-1000° C.) | wt % | 5 max. | 5 max. | 5 max. |
| Static adsorption (at 60% RH) | wt % | 21 | 21 | 21 |

The amount of Na in the treated stream was analyzed similar to example-1 and was found to be 0.04 ppm.

EXAMPLE-3

Process for Reducing Sodium Content in Di-sulfide Oil in Accordance with the Present Disclosure In this example, the treatment of the di-sulfide oil was carried out in the same manner as described in example-1, except that the alumina adsorbent that was used, had lower density and higher pore volume and higher surface area ($A_3$) [as compared to the alumina used in Example 1 ($A_1$)]. Characteristic attributes of the alumina adsorbent used in the present Example ($A_3$) have already been provided in Table-2.

The amount of Na in the treated stream by analyzed similar to example-1 and was found to be 0.01 ppm.

Sodium Removal Efficiency of the Adsorbents:

The sodium removal efficiency of the alumina adsorbents $A_1$, $A_2$ and $A_3$ is provided in Table-3.

TABLE 3

Sodium removal efficiency of various adsorbents:

| Sr. No | Di-sulfide oil | Adsorbent $Al_2O_3$ | Na in ppm | Removal Efficiency |
|---|---|---|---|---|
| 1. | Di-sulfide oil (untreated) | None | 3 | — |
| 2. | Treated di-sulfide oil | $A_1$ | 0.01 | 99.7% |
| 3. | Treated di-sulfide oil | $A_2$ | 0.04 | 98.7% |
| 4. | Treated di-sulfide oil | $A_3$ | 0.01 | 99.7% |

EXAMPLE-4

Process for Reducing Sodium Content in Di-sulfide Oil in Accordance with the Present Disclosure In this example, the treatment of the di-sulfide oil was carried out in the same manner as described in example-1, except that the liquid hourly space velocity (LHSV) of the di-sulfide oil stream was maintained at 2 hr$^{-1}$. The amount of Na in the treated di-sulfide oil was analyzed similar to example-1 and was found to be 0.04 ppm.

EXAMPLE-5

Laboratory Process for Reducing Sodium Content in Di-sulfide Oil in Accordance with the Present Disclosure In this example, the treatment of the di-sulfide oil was carried out in the same manner as described in example-1, except the liquid hourly space velocity (LHSV) of the di-sulfide oil stream was maintained at 5 hr$^{-1}$. The amount of Na in the treated di-sulfide oil was analyzed similar to example-1 and was found to be 0.1 ppm.

EXAMPLE-6

Process for Reducing Sodium Content in Di-sulfide Oil in Accordance with the Present Disclosure In this example, the treatment of the di-sulfide oil collected from a LPG desulfurization was carried out in the same manner as described in example-1, except that the temperature was maintained at 30° C. The amount of Na in the treated di-sulfide oil was analyzed similar to the example-1 and was found to be 0.01 ppm.

Inference:

After studying the results obtained in Examples 1 through 6, it was observed that:

1. By decreasing the density and increasing the porous volume of the alumina adsorbent, the sodium removal efficiency of the present process can be proportionately improved by keeping the liquid hourly space velocity (LHSV) of the oil stream and the temperature conditions of the column constant.
2. By reducing the liquid hourly space velocity (LHSV) of the oil stream, the sodium removal efficiency of the present process can be proportionately improved by keeping the type of alumina and the temperature conditions of the column constant.
3. Varying temperature in the ambient temperature range does not affect the sodium removal efficiency of the present process, when the liquid hourly space velocity (LHSV) of the oil stream, the type of alumina and the temperature conditions of the column are maintained at a constant.

Thus, passing a stream comprising di-sulfide oil having sodium level of 1 ppm, through alumina bed having average particle size ranging from 0.3 to 0.7 mm; pore volume ranging from 44.1 to 71.9 cm$^3$/100 g; surface area ranging from 195 to 331 m$^2$/g and density ranging from 543 to 829 kg/m$^3$ yielded sodium level below 0.1 ppm; where the liquid hourly space velocity (LHSV) was made to vary from 0.5 to 5.0 hr$^{-1}$, at a temperature ranging from 10 to 40° C.

TECHNICAL ADVANCEMENTS

The present disclosure relates to a process for removal of Na from di-sulfide oil and has several technical advancements, including but not limited to:

A very simple and efficient process for the removal of sodium from di-sulfide oil, a waste product obtained from LPG desulfurization process, An economic alternative to the existing anti-coking agent, for example di-methyl disulfide (DMDS), by providing di-sulfide oil having sodium level below 0.1 ppm which can be used very efficiently as an anti-coking agent in the thermal cracking of hydrocarbons with practically no change in the cracking product composition and/or energy requirement, An economic alternative to the existing sulfiding agents such as di-methyldisulfide (DMDS) used in the hydro-processing of non-edible vegetable oils to produce bio-jet or bio-diesel, and An economic alternative to the existing pre-sulfiding agent used in the hydrotreaters and hydrocrackers for the pre-sulfidization of the catalyst.

The numerical values mentioned for the various physical parameters, dimensions or quantities are only approximations and it is envisaged that the values higher/lower than the numerical values assigned to the parameters, dimensions or quantities fall within the scope of the invention, unless there is a statement in the specification specific to the contrary.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The invention claimed is:

1. A process for obtaining di-sulfide oil having sodium level below 0.1 ppm, said process comprising passing a stream comprising di-sulfide oil having sodium level of 1 ppm through an alumina bed packed in a column, at a liquid hourly space velocity (LHSV) ranging from 0.5 to 5.0 hr$^{-1}$ and at a pre-determined temperature to obtain a treated stream comprising di-sulfide oil having sodium level below 0.1 ppm.

2. The process as claimed in claim 1, wherein the liquid hourly space velocity (LHSV) ranges from 0.5 to 2 hr$^{-1}$.

3. The process as claimed in claim 1, wherein the liquid hourly space velocity (LHSV) ranges from 1.0 to 1.5 hr$^{-1}$.

4. The process as claimed in claim 1, wherein said pre-determined temperature varies from 10 to 40° C.

5. The process as claimed in claim 1, wherein said pre-determined temperature varies from 20 to 30° C.

6. The process as claimed in claim 1, wherein the treated stream comprises di-sulfide oil having sodium level below 0.05 ppm.

7. The process as claimed in claim 1, wherein the treated stream comprises di-sulfide oil having sodium level below 0.02 ppm.

8. The process as claimed in claim 1, wherein the treated stream comprises di-sulfide oil having sodium level of 0.01 ppm.

9. The process as claimed in claim 1, wherein the alumina is characterized by the following properties: average particle size ranging from 0.3 to 0.7 mm; pore volume ranging from 44.1 to 71.9 cm$^3$/100 g; surface area ranging from 195 to 331 m$^2$/g and density ranging from 543 to 829 kg/m$^3$.

* * * * *